United States Patent
Müller-Engel et al.

(10) Patent No.: US 6,849,758 B1
(45) Date of Patent: Feb. 1, 2005

(54) TREATMENT OF MIXTURES THAT CONTAIN AT LEAST ONE COMPOUND WITH AT LEAST ONE ETHYLENICALLY UNSATURATED GROUP

(75) Inventors: Klaus Joachim Müller-Engel, Stutensee (DE); Gerhard Nestler, Ludwigshafen (DE); Jürgen Schröder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/089,065

(22) PCT Filed: Oct. 2, 2000

(86) PCT No.: PCT/EP00/09630

§ 371 (c)(1),
(2), (4) Date: Apr. 5, 2002

(87) PCT Pub. No.: WO01/25173

PCT Pub. Date: Apr. 12, 2001

(30) Foreign Application Priority Data

Oct. 5, 1999  (DE) .......................................... 199 47 868

(51) Int. Cl.$^7$ .......................... C07C 69/00; C07C 69/34; C07C 64/52; C07C 67/00; C07C 67/36

(52) U.S. Cl. ........................ 560/196; 560/129; 560/204

(58) Field of Search .................................. 560/129, 190, 560/193, 196, 204

(56) References Cited

U.S. PATENT DOCUMENTS

| 3,271,296 A | 9/1966 | Gonzalez |
| 4,670,131 A | 6/1987 | Ferrell |
| 5,496,875 A | 3/1996 | Borzatta |

FOREIGN PATENT DOCUMENTS

| DE | 198 10 962 | 9/1999 |
| EP | 0 178 168 | 4/1986 |
| EP | 463 434 | 6/1991 |
| EP | 648 732 | 10/1994 |
| EP | 0 765 856 | 4/1997 |
| WO | 99/21893 | 5/1999 |

*Primary Examiner*—Johann Richter
*Assistant Examiner*—Karl J. Puttlitz
(74) *Attorney, Agent, or Firm*—Oblon, Spivak, McClelland, Maier & Neustadt, P.C.

(57) ABSTRACT

Mixtures containing monomers having at least one ethylenically unsaturated group are chemically and/or physically treated in the presence of the reaction products of alkylsuccinic anhydrides and stable N-oxyl radicals having a hydroxyl group.

13 Claims, No Drawings

TREATMENT OF MIXTURES THAT CONTAIN AT LEAST ONE COMPOUND WITH AT LEAST ONE ETHYLENICALLY UNSATURATED GROUP

The present invention relates to a process for the chemical and/or physical treatment of mixtures which contain at least one chemical compound having at least one ethylenically unsaturated group.

Chemical compounds which contain at least one ethylenically unsaturated group (monomers) are generally known and are important starting compounds for the preparation of polymers (for example by free radical polymerization) which are used, inter alia, as adhesives or as binders.

In the preparation of monomers, e.g. (meth)acrylic acid ("(meth)acryl-" is used in this publication as an abbreviation for "acryl- or methacryl-"), esters of (meth)acrylic acid, nitriles of (meth)acrylic acid or styrene, it is constantly necessary to subject mixtures which contain at least one monomer to chemical and/or physical treatments in a manner known per se.

The esterification of (meth)acrylic acid with monohydric or polyhydric alkanols (cf. for example EP-A 463 434) or the treatment of (meth)acrylic acid-containing mixtures by rectification (cf. for example DE-A 19 810 962 or EP-A 648 732) may be mentioned by way of example.

The disadvantage of these known processes for the chemical and/or physical treatment of mixtures which contain at least one chemical compound having at least one ethylenically unsaturated group is that monomers tend to undergo undesired free radical polymerization, and said processes are therefore usually carried out in the presence of free radical polymerization inhibitors. Known free radical polymerization inhibitors of this type are, for example, nitroxyl radicals (compounds which have at least one >N—O.— group) (cf. for example WO 9 921 893 and U.S. Pat. No. 4,670,131).

However, even when free radical polymerization inhibitors are present, undesired free radical polymerization of monomers frequently cannot be ruled out, and it is for this reason that, in addition to polymerization inhibitors, substances which keep undesired polymer formed in suspension, i.e. which are intended to prevent formation of polymer deposits on, for example, container walls, column bottoms or evaporator surfaces, are also frequently added in processes for the chemical and/or physical treatment of mixtures which contain at least one chemical compound having at least one ethylenically unsaturated group. Such substances are referred to as antifouling compositions (cf. for example U.S. Pat. No. 3,271,296).

Against this background, it is an object of the present invention to provide processes for the chemical and/or physical treatment of mixtures which contain at least one chemical compound having at least one ethylenically unsaturated group, which processes are carried out in the presence of substances which form, on the one hand, excellent free radical polymerization inhibitors and, on the other hand, excellent antifouling compositions.

We have found that this object is achieved by a process for the chemical and/or physical treatment of mixtures which contain at least one chemical compound having at least one ethylenically unsaturated group, which is carried out in the presence of at least one compound of the formulae (I) and (II)

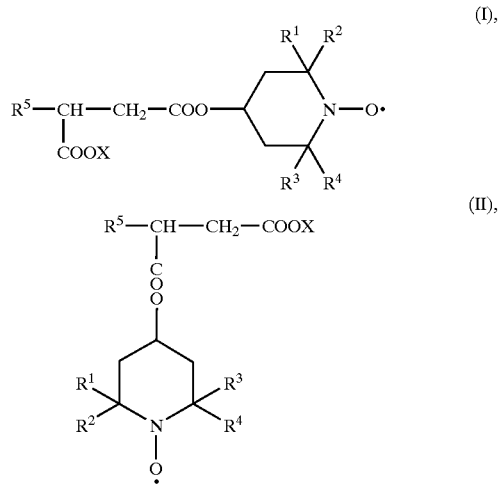

where X is H, an alkali metal and/or ammonium
$R^1$, $R^2$, $R^3$ and $R^4$, independently of one another, are each $C_1$- to $C_4$-alkyl and $R^5$ is $C_8$- to $C_{30}$-alkyl.

Compounds of the formulae (I) and (II) are disclosed, for example, in U.S. Pat. No. 5,496,875 and are recommended there as intermediates for the preparation of light and heat stabilizers for polymers.

According to the invention, suitable alkali metals X are in particular Na and K. $R^1$, $R^2$, $R^3$ and $R^4$, independently of one another, may be methyl, ethyl, n-propyl, isopropyl, n-butyl, isobutyl or tert-butyl. Accordingly, compounds (I) and (II) in which all radicals $R^1$, $R^2$, $R^3$ and $R^4$ are methyl or in which all radicals $R^1$, $R^2$, $R^3$ and $R^4$ are ethyl are also suitable according to the invention. $R^5$ may be, inter alia, $C_{15}$- to $C_{25}$-alkyl or $C_{17}$- to $C_{22}$-alkyl.

Preparation of compounds (I) and (II) is also described in U.S. Pat. No. 5,496,875.

For the preparation of the compounds

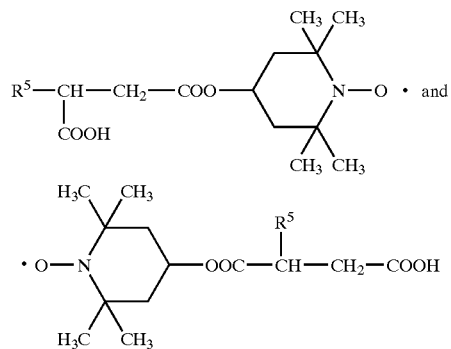

for example, the corresponding alkylsuccinic anhydrides can be reacted with 4-hydroxy-2,2,6,6-tetramethylpiperidine-N-oxyl (HTEMPO) at from 60 to 120° C. As a rule, the anhydride: N-oxyl molar ratio chosen for this purpose is from 0.8:1 to 1.5:1. Preferably, the reaction is carried out in the absence of a solvent. Where solvents are used, suitable ones are, for example, aromatic and/or aliphatic hydrocarbons, such as toluene, xylene and cyclohexane, as well as diphenyl ether, dialkyl phthalates, dialkylacetamides and N-alkylpyrrolidones. The reaction time is as a rule 0.1–5 hours. The synthesis is advantageously carried out under anhydrous conditions.

The alkylsuccinic anhydrides used may be, for example, compounds such as tetrapropenylsuccinic anhydride (e.g.

GP 103 from CONDEA), n-alkenylsuccinic anhydride having a number average molecular weight ($M_n$) of about 520 (e.g. GP 104 from CONDEA), or polyisobutenylsuccinic anhydride having an $M_n$ of about 850 (e.g. GP 105 from CONDEA) or having an $M_n$ of about 1400 (e.g. GP 106 from CONDEA).

In the novel process, possible compounds having at least one ethylenically unsaturated group may be, for example, styrene, butadiene, ethylene, vinyl ethers, vinyl esters, acrylic acid, methacrylic acid, alkyl esters (in particular $C_1$- to $C_8$-alkyl) of acrylic acid and methacrylic acid, methacrylonitrile, acrylonitrile or N-vinylpyrrolidone.

The compounds I and II to be used concomitantly according to the invention are employed as a rule in amounts of from 50 to 1000 ppm by weight, based on the amount of the monomers contained in the mixture to be treated according to the invention. Of course, the amount used may however also be up to 2000 or up to 3000 ppm by weight, on a corresponding basis. In suitable cases, however, it is of course also possible to use less than 50 ppm by weight.

The compounds (I) and (II) to be used according to the invention are preferably chosen so that, when used in the required amount, they are soluble in the mixture to be treated according to the invention.

According to the invention, mixtures of compounds I and II are generally used.

Of course, the compounds I and II can be used in the novel processes also as a mixture with other, known polymerization inhibitors and/or antifouling compositions. Suitable substances of this type include air, hydroquinone, hydroquinone monoethyl ether (MEHQ), paranitrosophenol, paramethoxyphenol, phenothiazine (PTZ), phenylenediamines, 4-hydroxy-2,2,6,6-tetramethylpiperidine-N-oxyl (HTEMPO), organic sulfonic acids (for example those published in EP-A 648 732), surfactants (for example those mentioned in DE-A 19810962) and all polymerization inhibitors stated in WO 9921893.

Advantageous combinations are, for example,
a) compounds I and II/PTZ;
b) compounds I and II/PTZ/MEHQ;
c) compounds I and II/PTZ/MEHQ/HTEMPO;
d) compounds I and II/MEHQ/HTEMPO;
e) compounds I and II/MEHQ;
f) compounds I and II/MEHQ/HTEMPO.

The novel chemical treatment may be, for example, a conventional chemical reaction of a monomer with retention of the at least one ethylenically unsaturated group. The esterification of, for example, (meth)acrylic acid with alkanols has already been mentioned as an example. The novel physical treatment may be, for example, an extraction, distillation, rectification, absorption or crystallization process.

The mixtures to be treated according to the invention may be, for example, pure monomer mixtures as well as mixtures of monomers and of substances other than monomers. As a rule, the weight fraction of the monomers in the mixtures to be treated according to the invention is at least 5 or at least 10 or at least 15 or 25 or 40% by weight.

In particular, the mixture to be treated according to the invention may comprise ≧95% by weight of (meth)acrylic acid.

The novel process is suitable, inter alia, for isolating, by rectification, (meth)acrylic acid from a mixture containing, as main components, (meth)acrylic acid and an organic liquid having a higher boiling point than (meth)acrylic acid, as described in DE-A 19810962. The compounds I and II to be used according to the invention can be fed to the isolation by rectification at all points where WO 9921893 recommends the addition of a surfactant. If required, they can be used together with surfactants. Frequently, the compounds I and II are added in solution in (meth)acrylic acid. Moreover, the novel procedure is also suitable in the case of the processes for the purification of crude (meth)acrylic acid by distillation, as described in EP-A 35 648 732. The compounds I and II to be used according to the invention can be employed alternatively to or together with the sulfonic acids and polymerization inhibitors used in EP-A 648 732.

EXAMPLES a) In each case 1 g of a crude acrylic acid which has been obtained by catalytic gas-phase oxidation of acroleine according to Example B1 of DE-A 4 302 991 and subsequent working-up of the reaction gas mixture according to Example B1 of DE-A 2 136 396 and which has been stabilized with 300 ppm by weight of phenothiazine was mixed, under conditions of saturation with air, with various amounts of different polymerization inhibitors and/or antifouling compositions in a test tube. Thereafter, in each case 5 mg of azobisisobutyronitrile (free radical polymerization initiator) were added and the samples were heated open at 60° C. in a water bath.

The time taken for the sample to begin to polymerize was then determined (detector: the liberated heat of polymerization). The times obtained as a function of added polymerization inhibitor and/or antifouling composition are shown in Table 1 below. The stated amounts are based on the total amount of the mixture. When no additional inhibitor or antifouling composition was added (i.e. the starting crude acrylic acid was used alone), the time was 19 minutes.

TABLE 1

| Composition added | Time (min) |
| --- | --- |
| 300 ppm by weight of GP 103 (from CONDEA) | 19 |
| 600 ppm by weight of GP 104 (from CONDEA) | 20 |
| 300 ppm by weight of HTEMPO | 25 |
| 300 ppm by weight of GP 103 (from CONDEA) and 300 ppm by weight of HTEMPO | 24 |
| 600 ppm by weight of the reaction product of GP 103 (from CONDEA) with HTEMPO | 24 |

It is noteworthy that the inhibitory effect of HTEMPO on the free radical polymerization is not impaired by the chemical bonding of GP 103.

b) 137 g/h of a crude acrylic acid which had been obtained by catalytic gas-phase oxidation of acroleine according to Example B1 of DE-A 4 302 991 and subsequent working-up of the reaction gases according to Example B1 of DE-A-2 136 396 were fed continuously, via the evaporator, into a glass rectification unit which was to be operated continuously and whose evaporator was a convection reboiler which was heated by means of a metallic, electrically heatable element, 1100 ppm by weight of aminoguanidine bicarbonate (as an aldehyde scavenger) and the polymerization inhibitors and/or antifouling compositions to be tested (cf. Table 2) having been added to said crude acrylic acid before it was fed into the evaporator. The temperature in the reboiler was 78° C. and the pressure at the top of the column was 100 mbar. The column was 1.5 m long and was filled with raschig rings (5 mm, glass).

The mixture removed via the column and comprising low boilers contained in the crude acrylic acid, such as acetic acid and water, and small amounts of acrylic acid was condensed. 25 g/h of the condensate were removed and the remainder was recycled as reflux to the top of the column. To stabilize the column, a solution of 5000 ppm by weight of phenothiazine in pure acrylic acid was added at the top of said column (20 ml/h). The bottom product substantially freed from the low boilers was removed from the evaporator under level control. During the rectification, deposition occurred on the heating element, the amount of which was weighed after an operating time of, in each case, 40 hours for each polymerization inhibitor and/or antifouling composition to be tested. The results obtained are shown in Table 2.

TABLE 2

| Composition added | Deposition |
|---|---|
| 100 ppm by weight of HTEMPO | 7.7 g |
| 100 ppm by weight of HTEMPO and 100 ppm by weight of GP 103 (from CONDEA) | 4.2 g |
| 200 ppm by weight of the reaction product of GP 103 (from CONDEA) with HTEMPO | 1.4 g |
| 400 ppm by weight of the reaction product of GP 104 (from CONDEA) with HTEMPO | 1.1 g |
| 600 ppm by weight of the reaction product of GP 105 (from CONDEA) with HTEMPO | 1.2 g |

It is noteworthy that the compounds I and II to be used according to the invention are not only outstanding polymerization inhibitors but also excellent antifouling compositions.

What is claimed is:

1. A process comprising inhibiting free radical polymerization in a mixture comprising at least one chemical compound having at least one ethylenically unsaturated group, wherein inhibiting free radical polymerization is carried out by mixing at least one compound of the formulae (I) or (II) with said mixture.

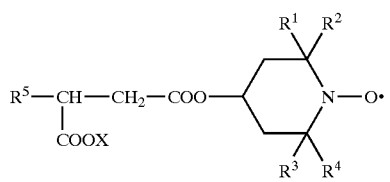

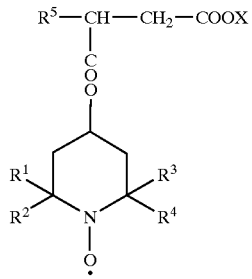

where X is H, an alkali metal or ammonium, $R^1$, $R^2$, $R^3$ and $R^4$, independently of one another, are each $C_1$- to $C_4$-alkyl and $R^5$ is $C_8$- to $C_{30}$-alkyl.

2. A process as claimed in claim 1, wherein the at least one chemical compound having at least one ethylenically unsaturated group is selected from the group consisting of acrylic acid, methacrylic acid, acrylonitrile, methacrylonitrile, styrene, an ester of acrylic acid and an ester of methacrylic acid.

3. A process as claimed in claim 1, wherein the mixture comprises (meth)acrylic acid and an organic liquid having a higher boiling point than (meth)acrylic acid.

4. A process as claimed in claim 1, wherein the mixture comprises $\geq 95\%$ by weight of (meth)acrylic acid.

5. A process as claimed in claim 1, further comprising at least one of rectification, extraction or absorption.

6. A process as claimed in claim 1, wherein $R^1$, $R^2$, $R^3$ and $R^4$ are either all methyl or all ethyl.

7. A process as claimed in claim 1, wherein X is H.

8. A process as claimed in claim 1, which is carried out at from 100 to 200° C.

9. A process as claimed in claim 1, which is carried out at $\leq 100$ mbar.

10. A mixture comprising at least one chemical compound having at least one ethylenically unsaturated group and at least one compound of formulae (I) or (II)

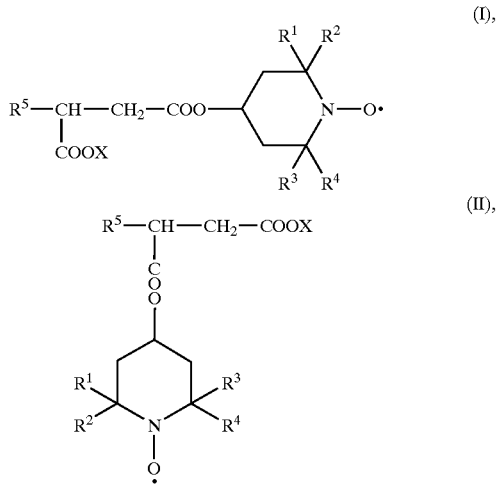

where X is H, an alkali metal or ammonium, $R^1$, $R^2$, $R^3$ and $R^4$, independently of one another, are each $C_1$- to $C_4$-alkyl and $R^5$ is $C_8$- to $C_{30}$-alkyl.

11. A mixture as claimed in claim 10, where said at least one chemical compound having at least one ethylenically unsaturated group is at least one selected from the group consisting of acrylic acid, methacrylic acid, acrylonitrile, methacrylonitrile, styrene, esters of acrylic acid and esters of methacrylic acid.

12. A mixture as claimed in claim 10, wherein $R^1$, $R^2$, $R^3$ and $R^4$ are either all methyl or all ethyl.

13. A process comprising inhibiting free radical polymerization in a mixture comprising at least one chemical compound having at least one ethylenically unsaturated group, wherein inhibiting free radical polymerization carried out by mixing at least one compound which is obtained by reacting an alkylsuccinic anhydride having a number average molar mass of from 212 to 1400 with 4-hydroxy-2,2,6,6-tetramethylpiperidin-N-onyl, with said mixture.

* * * * *